(12) United States Patent
Brodkin et al.

(10) Patent No.: US 6,375,729 B1
(45) Date of Patent: Apr. 23, 2002

(54) MACHINABLE GLASS-CERAMICS

(75) Inventors: Dmitri Brodkin, West Orange; Carlino Panzera, Belle Mead; Paul Panzera, Mt. Holly, all of NJ (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

(21) Appl. No.: 09/527,196

(22) Filed: Mar. 17, 2000

Related U.S. Application Data

(60) Provisional application No. 60/125,506, filed on Mar. 19, 1999.

(51) Int. Cl.$^7$ .......................... C03C 10/04; A61C 5/08; A61C 13/083
(52) U.S. Cl. .......................... 106/35; 264/16; 264/19; 264/20
(58) Field of Search .............................. 106/35; 264/16, 264/19, 20; 301/5, 6, 7, 3, 17

(56) References Cited

U.S. PATENT DOCUMENTS

| | | | |
|---|---|---|---|
| 3,325,265 A | 6/1967 | Stookey | 501/9 |
| 3,732,087 A | 5/1973 | Grossman | 501/9 |
| 3,801,295 A | 4/1974 | Beall | 501/9 |
| 3,839,055 A | 10/1974 | Grossman | 501/9 |
| 3,905,824 A | 9/1975 | Grossman | 501/9 |
| 3,985,531 A | 10/1976 | Grossman | 501/9 |
| 4,239,520 A | 12/1980 | Grossman | 501/9 |
| 4,431,420 A * | 2/1984 | Adair | 433/199 |
| 4,467,039 A | 8/1984 | Beall | 501/3 |
| 4,650,418 A | 3/1987 | Blair | 433/203.1 |
| 4,652,312 A | 3/1987 | Grossman | 106/35 |
| 4,731,394 A | 3/1988 | Vogel | 523/115 |
| 4,744,757 A | 5/1988 | Adair | 433/180 |
| 4,747,876 A | 5/1988 | Hakamatsuka | 106/35 |
| 4,767,725 A * | 8/1988 | Mizutani et al. | 501/3 |
| 4,789,649 A | 12/1988 | Abert | 501/3 |
| 4,799,887 A | 1/1989 | Hakamatsuka | 433/212.1 |
| 4,935,387 A | 6/1990 | Beall | 501/3 |
| 5,034,353 A * | 7/1991 | Shibuya et al. | 501/3 |
| 5,066,619 A | 11/1991 | Kasuga | 501/3 |
| 5,246,889 A | 9/1993 | Kasuga | 501/3 |
| 5,346,396 A | 9/1994 | Hakamatsuka | 433/208 |
| 5,507,962 A | 4/1996 | Jahanmir | 252/219.3 |
| 5,698,482 A | 12/1997 | Frank | 501/10 |
| 5,968,856 A | 10/1999 | Schweiger | 501/7 |
| 6,033,222 A | 3/2000 | Schneider, II | 433/203.1 |

OTHER PUBLICATIONS

Thompson, J.Y., Bayne, S.C., Heymann, H.O., Mechanical Propertiesx of New Mica–Based Machinable Glass Ceramic for CAD/CAM Restorations. The Journal of Prosthetic Dentistry, Dec. 1996, pp. 619–623.

Grossmand, D.G., Machinable Glass–Ceramics Based on Tetrasilicic Mica. The Journal of the American Ceramic Society. Sep., 1972, vol. 55, No. 9. pp. 446–449.

* cited by examiner

*Primary Examiner*—C. Melissa Koslow
(74) *Attorney, Agent, or Firm*—Ann M. Knab, Esq.

(57) ABSTRACT

Micaceous glass-ceramics are useful in the fabrication of single and multi-unit dental restorations including but not limited to orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors by machining the glass-ceramic using CAM/CAM devices. The micaceous glass-ceramics are provided in a plurality of shades and colors to adequately match the colors and shades of teeth found in 95% or more of the human population.

17 Claims, No Drawings

MACHINABLE GLASS-CERAMICS

CROSS-REFERENCE TO RELATED APPLICATIONS

This application claims priority to Provisional Application Serial No. 60/125,506 filed on Mar. 19, 1999 which is hereby incorporated by reference.

FIELD OF THE INVENTION

This invention relates generally to a glass powder, which is crystallizable and forms a sintered micaceous glass-ceramic in a plurality of shades and more specifically to micaceous glass ceramics, which are machinable into various dental articles by conventional tools. This material is especially useful for the fabrication of dental restorations using computer assisted design/computer assisted milling (CAD/CAM) devices.

BACKGROUND OF THE INVENTION

Micaceous glass-ceramic materials (i.e. glass-ceramics comprising a crystalline phase that belongs to the mica family such as tetrasilic fluormicas or fluorophlogopite micas) are known to exhibit excellent machinability. However, their use as CAD/CAM materials for dentistry is limited by the inability to produce the required range of shades and translucency paramount for esthetically sound restorations. This severely inhibits widespread use of micaceous materials as dental restoratives considering that the driving force for all-ceramic restorations is esthetics superior to that of porcelain fused-to-metal (PFM) restorations. For example, Dicor MGC, available from Dentsply International Inc., Caulk Division, (located in Milford, DE) is a commercially available micaceous dental ceramic for use in CAD/CAM devices, but it is supplied in only two modifications, Dicor MGC—Light and Dicor MGC—Dark. Other limitations of micaceous glass-ceramics include high solubility and low strength in comparison to other dental ceramics. One such example is ProGlass™ ceramic available from CAD/CAM Ventures LLC, (located in Irving, Tex.), which is a sugary-white mica-containing material exhibiting a flexure strength of about 100 to about 150 MPa and a solubility of about 1 mg/cm$^2$ (1000 $\mu$m/cm$^2$).

At the same time, micaceous glass-ceramics exhibit far superior machinability compared to other CAD/CAM ceramics such as sanidine-based Vita Mark II, available from Vita Zahnfabrik (Germany) and leucite-based Pro-Cad from Ivoclar (Lichtenstein), as set forth in "Mechanical Properties of a New Mica-Based Machinable Glass Ceramic For CAD/CAM Restorations" by J. Y. Thompson et al., The Journal of Prosthetic Dentistry, 1996, Vol. 76, No. 6,619–623 and "Machinable Glass-Ceramics Based on Tetrasilicic Mica" by D. G. Grossman, Journal of Am.Cer.Soc., 1972, Vol. 55, No. 9. The latter two above-mentioned ceramics can be machined by diamond tools only and require wet processing in contrast to micaceous glass-ceramics such as ProGlass™ which can be machined by carbide tooling using dry processing which is much more cost-effective. In addition, micaceous glass-ceramics can be much more translucent than very opaceous sanidine glass-ceramics.

U.S. Pat. Nos. 4,652,312, 4,431,420 and 5,246,889 are each directed to mica-containing ceramics that are formed from glass compositions and are shaped as glass and converted into micaceous glass-ceramics by conventional volume crystallization techniques. Each process involves melting glass batches, casting the glass melts into molds, and crystallizing the glass into micaceous glass-ceramics. There is no discussion providing how to achieve adequate colors and shades to accurately match the color of a person's tooth or how to control the shading of mica containing glass-ceramics. Any mention of colorants appears to be directed to adding the colorants to the glass batch prior to melting. Such process does not effectively control the color of the resulting glass-ceramic. Furthermore, each of the processes appears to effect crystallization by performing bulk or volume crystallization. It is difficult to control the color of the micaceous glass-ceramics when utilizing volume crystallization. None of the prior art is concerned with the need to provide a variety of colors and shades to adequately match the color and shade of a patient's teeth.

It is desirable to provide a variety of shades of micaceous glass-ceramics in order to fabricate restorations that closely and accurately match the teeth in a patient's mouth. It is preferable to provide an efficient and effective method of producing a variety of shades of micaceous glass-ceramics. It is beneficial to provide micaceous glass-ceramics that are machinable and that come in a variety of shades.

SUMMARY OF THE INVENTION

These and other objects and advantages are accomplished herein by the micaceous glass-ceramics comprising silica, magnesium oxide and fluorine in addition to other components listed below. The glass-ceramics are useful in the fabrication of single and multi-unit dental restorations including but not limited to orthodontic appliances, bridges, space maintainers, tooth replacement appliances, splints, crowns, partial crowns, dentures, posts, teeth, jackets, inlays, onlays, facing, veneers, facets, implants, abutments, cylinders, and connectors by machining the glass-ceramic using CAM/CAM devices. The micaceous glass-ceramics are provided in a shade and color selected from a plurality of shades and colors to adequately match the colors and shades of teeth found in 95% or more of the human population.

In accordance with one embodiment directed to the process of making the glass-ceramics, the batch ingredients of the compositions are melted at a temperature in the range of about 1200° to about 1650° C., for a time in the range of about 0.5 to about 8 hours, thereafter it is quenched, and pulverized into powder. Pigments, opacifiers, fluorescing agents and the like are mixed with the powder. The powder is then used to form net-shaped or block-shaped pre-forms or blanks to be used in CAD/CAM devices. Blanks are dry-pressed and sintered using a one- or two-step heating cycle at a temperature in the range of about 600° to about 1200° C. and for a time in the range of about 0.5 to about 4 hours for each step in the cycle. The sintering is preferably conducted in a vacuum. Occurring simultaneously with sintering, surface crystallization of the starting glass powder yields the amount of mica phase of at least thirty volume percent (30 vol. %) required for machinability as well as strength.

DETAILED DESCRIPTION OF THE INVENTION

As will be appreciated, the present invention provides glass-ceramic compositions comprising a glassy matrix and one or more micaceous phases (e.g., tetrasilic flourmica, fluorophlogopite mica and the like). The glass-ceramics are useful in the fabrication of dental restorations. The micaceous glass-ceramic compositions contain inter alia, silica, magnesium oxide and fluorine in the ranges given in Table 1 below. The glass-ceramic compositions have a combination of properties including high strength and chemical durability useful for dental restorations. The glass-ceramics have good machinability, i.e., the ability to be cut or milled by a cutting tool into a dental restorative shape that accurately depicts the original shape of the tooth to be restored or replaced.

In an important aspect herein, the micaceous glass-ceramics are provided in a shade and color selected from a plurality of shades and colors to adequately match the colors and shades of teeth found in 95% or more of the human population. The shades and colors of the glass-ceramics provide the dental technician with the ability to closely and effectively match the color and shade of the patient's tooth or teeth abutting or adjacent to the tooth or teeth that is/are being restored or replaced.

TABLE 1

Compositions of the starting glass powder

| Oxide | Mole % | Wt % Range 1 | Wt % Range 2 |
|---|---|---|---|
| $SiO_2$ | 30–65 | 43–72 | 43–72 |
| $Al_2O_3$ | 0–7 | 3–14 | 0–3 |
| $B_2O_3$ | 0–3 | 0–3 | 0–3 |
| ZnO | 0–3 | 0–3 | 0–3 |
| CaO | 0–5 | 0–7 | 0–3 |
| MgO | 15–33 | 10–30 | 10–30 |
| $TiO_2$ | 0–3 | 0–3 | 0–3 |
| BaO + SrO | 0–3 | 0–5 | 0–5 |
| $Li_2O$ | 0–3 | 0–3 | 0–3 |
| $K_2O$ | 0–10 | 0–7 | 7–19 |
| $Na_2O$ | 0–7 | 0–3 | 0–3 |
| $CeO_2 + La_2O_3 + Tb_4O_7$ | 0–1 | 0–2 | 0–2 |
| ZrO2 | 0–4 | 0–10 | 0–10 |
| F | 14–25 | 5–10 | 5–10 |

In accordance with one embodiment of the method of the invention, the shaded micaceous glass-ceramics are manufactured by admixing pigments and other additives to the starting glass powder. The powder is formed into pre-forms or blanks and the blanks are concurrently sintered and crystallized. The resulting shaded blanks of various shades and translucency levels are consistent with current all-ceramic or porcelain-fused-to-metal (PFM) dental porcelain systems. The pre-forms or blanks may be machined into a dental restoration using a CAD/CAM device.

In accordance with the process, the glass compositions within the ranges given in Table 1 are melted at a temperature in the range of about 1200° to about 1650° C. and for a time in the range of about 0.5 to about 8 hours, thereafter quenched, and pulverized into powder. This powder is sieved to obtain the required particle size and mixed with conventional additives such as pigments, opacifiers, and fluorescing agents, which will produce various colors, shades and translucency levels after sintering and concurrent crystallization have been performed. The powder that contains the additives is then used to form net-shaped or block-shaped pre-forms or blanks to be used in CAD/CAM devices. The blanks are dry-pressed and sintered using a one- or two-step heating cycle at a temperature in the range of about 600° to about 1200° C. and for a time in the range of about 0.5 to about 4 hours for each step in the cycle. The sintering is preferably conducted in a vacuum atmosphere. Occurring simultaneously with sintering, surface crystallization of the starting glass powder yields an amount of mica phase of at least thirty volume percent (30 vol %) required for machinability as well as strength. Copending commonly assigned U.S. application Ser. No. 09/458,919, filed on Dec. 10, 1999, and U.S. Pat. No. 5,968,856 to Schweiger discuss volume crystallization and surface crystallization of lithium disilicate glass-ceramics and are hereby incorporated by reference.

In mass-production of CAD/CAM blanks, uniaxial pressing or other forming techniques are utilized, e.g. CIP/HIP route whereby green bodies are formed in a CIP (Cold Isostatic Press) and subsequently sintered under pressure in an HIP (Hot Isostatic Press). As an alternative to the CIP method, the powder can be mixed with binder and pelletized or extruded. Useful CAD/CAM devices include the CEREC™ machine (available from Siemens AG), the PRO-CAM™ machine (available from CAD CAM Ventures LLC in Irving, Tex.) or copy-milling devices such as the Celay™ machine (available from Mikrona Technologie AG).

Essential for the present invention is an F content in excess of about 14 mole percent (about 5 weight percent). Besides being a constituent of fluormicas, F facilitates surface crystallization. Other ingredients that favor surface crystallization are $B_2O_3$, $P_2O_5$, BaO and $Li_2O$.

Essential for the present invention is the volume fraction, size and aspect ratio of the mica phase in the resultant sintered glass-ceramic. The larger the mica plates and the higher their aspect ratio, the lower the volume fraction of mica that is required to attain machinability. An aspect ratio, i.e., ratio of thickness to length, of the mica plate of $\geq 2$ is preferred. At least thirty volume percent (30 vol. %) of mica is required to attain machinability. At least thirty volume percent (30 vol. %) of the residual glass phase is required for sinterability. Therefore, the mica content is between about 30 and about 70 volume percent, and preferably between about 40 and about 60 volume percent.

Some of the compositions of the present invention are extremely reactive and will dissolve additives (e.g., pigments and fluorescing agents) during sintering of the CAD/CAM blocks. In this case, it was found that using coarser additives (e.g., pigments or fluorescing agents) substantially alleviated this problem. Normally, these additives (pigments and fluorescing agents) have an average particle size of about 4 to about 8 microns. For most reactive compositions, it was found to be critical to use additives of average particles size equal to or exceeding 15 microns. It is believed that, at the same time, particles exceeding 60 microns will compromise strength. Thus, special care should be taken to remove particles greater than 60 microns. Preferably, the average size of the additives is in the range of about 15 to about 35 microns, and more preferably in the range of about 20 to about 30 microns.

Application of pressure during sintering of blanks such as in the CIP/HIP route described above is more expensive than vacuum sintering of uniaxially pressed blanks but may be extremely beneficial in some cases. For example, the CIP/HIP route allows consolidation of powders having high pigment load, or powders yielding high mica content upon crystallization, or powders having high $ZrO_2$ content.

Extremely beneficial, especially for larger high aspect ratio mica, is post-machining heat treatment of dental restorations at temperatures between the glass transition temperature (GTT) and the dilatometric softening point (DSP). This heat-treatment affects surface crack healing and increases structural integrity of the restorations.

In addition to fluormicas, other phases can be present such as cordierite, apatite, spodumene and zirconia. Consequently the expansion of the resulting glass-ceramic can be varied in the range of about 7 to about $12 \times 10^{-6}/°C$.

A coating is preferably applied over the core material manufactured from the micaceous glass-ceramic to provide an aesthetically pleasing surface. A suitable coating is a ceramic, glass-ceramic, a glass, a glaze and/or a composite material. It is advantageous that the coating has a coefficient of thermal expansion slightly less than the thermal expansion of the core material. The coating is typically applied by sintering the ceramic, glass-ceramic, glass, glaze a composite material onto the micaceous glass-ceramic core.

The following examples illustrate the invention.

Example 1

A starting glass composition corresponding to the composition set forth in Table 2 below was batched from conventional raw ingredients and melted at 1400° C. for 4 hours in a coarse-grained alumina crucible. The glass melt was quenched into water. The quenched glass was dried and milled into powder. The powder was screened to −200 mesh. Commercial pigments and fluorescing agents (yellow from Cerdec Co. (Washington, Pa.), pink from Engelhard Corp. (Iselin, N.J.) and jet black from Standard Ceramic Supply Co. (Carnegie, Pa.)) were added to and blended with the powder. The powder was dry-pressed into $18 \times 18 \times 25$ mm$^3$ blocks. The blocks were fired in a vacuum of 20 torr using a two-step heating cycle at 10° C./min to 650° C. and held for 2 hours at this temperature and 10° C./min to 1100° C. and held for 4 hours at this temperature. The blocks were sectioned into bars for three-point bend strength tests and small squares for solubility measurements according to ISO 9693 solubility testing standards. The measurements are listed in Table 2 below.

Example 2

A starting glass composition corresponding to composition set forth in Table 2 below was batched from conventional raw ingredients and melted at 1400° C. for 4 hours in a coarse-grained alumina crucible. The glass melt was quenched into water. The quenched glass was dried and milled into powder. The powder was screened to −200 mesh. Commercial pigments and fluorescing agents were used in concentrations given in Table 3 below. Since it is known that all dental shades can be produced by varying combinations of three basic pigments. i.e., yellow, red (or pink) and blue (or gray or black), the glass-ceramic of this example was shaded using both individual yellow, pink and black pigments and their combinations. Yellow pigments from Cerdec (Washington, Pa.), pink pigments from Engelhard Corp. (Iselin, N.J.) and jet black pigments from Standard Ceramic Supply Co. (Carnegie, Pa.) were used. The powder formulations were pressed into 2.5 gram disks and fired in a vacuum of 20 torr using a two-step heating cycle at 10° C./min to 650° C. and held for 2 hours at this temperature and 10° C./min to 1100° C. and held for 4 hours at this temperature. The resulting shades were evaluated using the ColorTec-SCM™ color computer from ColorTec Corp. (Clinton, N.J.) and were found appropriate for simulating the color and shade of a person's teeth.

Example 3

Blocks of lightly shaded glass-ceramics of Example 2 were sent to CAD CAM Ventures LLC (Irving, Tex.) and to DentalMatic Technologies Inc. (Sainte-Laurent, Quebec, Canada) to be evaluated for machinability. They were machined into shapes roughly approaching that of a dental coping. The machinability was evaluated as satisfactory.

TABLE 2

Compositions of glass-ceramics in Examples 1 and 2

| Oxide | Wt % Example 1 | Wt % Example 2 |
|---|---|---|
| $SiO_2$ | 40.8 | 61.0 |
| $Al_2O_3$ | 11.6 | 0.5 |
| $B_2O_3$ | 0 | 0 |
| ZnO | 0 | 0 |
| CaO | 5.5 | 0 |
| MgO | 27.4 | 17.2 |
| $TiO_2$ | 0 | 0 |
| BaO | 0 | 0 |
| $Li_2O$ | 0 | 0 |
| $K_2O$ | 1.5 | 13.1 |
| $Na_2O$ | 0 | 0 |
| $CeO_2$ | 0 | 0 |
| $ZrO2$ | 8.3 | 5 |
| F | 8.6 | 5.6 |
| 3-Pt bend strength (MPa) | 196 ± 24 | >100 |
| ISO 9693 Solubility $\mu g/cm^2$ | 8 | <100 |
| CTE (25°–500° C.) | $8° \times 10^{-6}/°C.$) | Not Measured |

TABLE 3

Example 2 powder with the addition of pigments.

| Glass powder of example 2 Wt % | Yellow 41720 Wt % | Pink D320 Wt % | Jet Black K-60 Wt % | CIE L*a*b* Light Source: D65-10° | |
|---|---|---|---|---|---|
| 99.2687 | 0.7313 | | | L* | 53.31 |
| | | | | a* | −2.47 |
| | | | | b* | 21.33 |
| | | | | C* | 21.47 |
| | | | | h* | 96.62 |
| 99.6693 | | 0.3307 | | L* | 55.461 |
| | | | | a* | 2.10 |
| | | | | b* | 0.22 |
| | | | | C* | 2.11 |
| | | | | h* | 6.06 |

TABLE 3-continued

Example 2 powder with the addition of pigments.

| Glass powder of example 2 Wt % | Yellow 41720 Wt % | Pink D320 Wt % | Jet Black K-60 Wt % | CIE L*a*b* Light Source: D65-10° | |
|---|---|---|---|---|---|
| 99.995 | | | 0.005 | L* | 54.67 |
| | | | | a* | −0.31 |
| | | | | b* | 0.08 |
| | | | | C* | 0.32 |
| | | | | h* | 164.84 |
| 98.6 | 1.4 | | | | |
| 99.3 | | 0.7 | | | |
| 99.99 | | | 0.01 | | |
| 98.933 | 0.7313 | 0.3307 | 0.005 | | |
| 98.59 | 0.7 | 0.7 | 0.01 | | |

The glass-ceramics of the invention have the capability to provide a wide selection of shades and colors for matching the shades and colors of a person's teeth. The glass-ceramics are readily machinable and provide high strength and chemical durability to the dental restorations made therefrom.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of making a micaceous dental material comprising:
   melting a starting glass composition at temperatures within the range of about 1200 to about 1650° C.;
   quenching the glass melt;
   pulverizing the quenched glass into a powder;
   forming the glass powder into pre-forms;
   sintering the pre-forms to convert the glass into a glass-ceramic dental material;
and
   milling the pre-forms into a dental restoration.

2. The method of claim 1 further comprising adding one or more additives selected from pigments, fluorescing agents, opacifying agents and mixtures thereof to the glass powder prior to shaping the powder into pre-forms.

3. The method of claim 2 wherein the additives have an average particle size equal to or exceeding about 15 microns and not larger than about 60 microns.

4. The method of claim 3 wherein the average particle size of the additives is in the range of about 15 to about 35 microns.

5. The method of claim 3 wherein the average particle size of the additives is in the range of about 20 to about 30 microns.

6. A method of making a micaceous dental material comprising:
   melting a starting glass composition at temperatures within the range of about 1200 to about 1650° C.;
   quenching the glass melt;
   pulverizing the quenched glass into a powder;
   forming the glass powder into pre-forms; and
   sintering the pre-forms to convert the glass into a glass-ceramic dental material;
   wherein the micaceous glass-ceramic comprises:
      about 43 to about 72 weight % $SiO_2$;
      about 3 to about 14 weight % $Al_2O_3$;
      about 10 to about 30 weight % MgO; and
      about 5 to about 10 weight % F.

7. The method of claim 6 wherein the micaceous glass-ceramic further comprises:
   up to about 3 weight % $B_2O_3$;
   up to about 3 weight % ZnO;
   up to about 7 weight % CaO;
   up to about 5 weight % BaO and SrO;
   up to about 3 weight % $Li_2O$;
   up to about 7 weight % $K_2O$;
   up to about 3 weight % $Na_2O$;
   up to about 2 weight % $CeO_2$, $La_2O_3$ and $Tb_4O_7$;
   up to about 3 weight % $TiO_2$;and
   up to about 10 weight % $ZrO_2$.

8. The method of claim 6 wherein the glass-ceramic comprises at least about thirty volume percent of mica.

9. A method of making a micaceous dental material comprising:
   melting a starting glass composition at temperatures within the range of about 1200 to about 1650° C.;
   quenching the glass melt;
   pulverizing the quenched glass into a powder;
   forming the glass powder into pre-forms; and
   sintering the pre-forms to convert the glass into a glass-ceramic dental material;
   wherein the micaceous glass-ceramic comprises:
      about 43 to about 72 weight % $SiO_2$;
      about 7 to about 19 weight % $K_2O$;
      about 10 to about 30 weight % MgO; and
      about 5 to about 10 weight % F.

10. The method of claim 9 wherein the micaceous glass-ceramic further comprises:
   up to about 3 weight % $Al_2O_3$;
   up to about 3 weight % $B_2O_3$;
   up to about 3 weight % ZnO;
   up to about 3 weight % CaO;
   up to about 5 weight % BaO and SrO;
   up to about 3 weight % $Li_2O$;
   up to about 3 weight % $Na_2O$;
   up to about 2 weight % $CeO_2$, $+La_2O_3+Tb_4O_7$;
   up to about 3 weight % $TiO_2$;and
   up to about 10 weight % $ZrO_2$.

11. The method of claim 9 wherein the glass-ceramic comprises at least about thirty volume percent of mica.

12. A method of making a micaceous dental material comprising:

melting a starting glass composition at temperatures within the range of about 1200 to about 1650° C.;

quenching the glass melt;

pulverizing the quenched glass into a powder;

forming the glass powder into pre-forms; and sintering the pre-forms to convert the glass into a glass-ceramic dental material;

wherein sintering is conducted under a vacuum.

13. A method of making a micaceous dental material comprising:

melting a starting glass composition at temperatures within the range of about 1200 to about 1650° C.;

quenching the glass melt;

pulverizing the quenched glass into a powder;

adding one or more additives selected from pigments, fluorescing agents, opacifying agents and mixtures thereof to the glass powder;

forming the glass powder into pre-forms;

sintering the pre-forms to convert the glass into a glass-ceramic dental material;

and milling the pre-forms into a dental restoration.

14. A micaceous dental restoration made from the method of claim 1.

15. The micaceous dental restoration of claim 14 selected from the group consisting of an orthodontic appliance, bridge, space maintainer, tooth replacement appliance, splint, crown, partial crown, denture, post, tooth, jacket, inlay, onlay, facing, veneer, facet, implant, abutment, cylinder, and connector.

16. A micaceous dental restoration made from the method of claim 6.

17. The micaceous dental restoration of claim 16 selected from the group consisting of an orthodontic appliance, bridge, space maintainer, tooth replacement appliance, splint, crown, partial crown, denture, post, tooth, jacket, inlay, onlay, facing, veneer, facet, implant, abutment, cylinder, and connector.

* * * * *